US010660661B2

(12) United States Patent
Beyer

(10) Patent No.: US 10,660,661 B2
(45) Date of Patent: May 26, 2020

(54) COMBINED DISTRACTION AND COMPRESSION CLAMP FOR SURGICAL OPERATIONS

(71) Applicant: Neo Medical SA, La Villette (CH)

(72) Inventor: Morten Beyer, Rødkærsbro (DK)

(73) Assignee: Neo Medical S.A., La Villette (CH)

( * ) Notice: Subject to any disclaimer, the term of this patent is extended or adjusted under 35 U.S.C. 154(b) by 113 days.

(21) Appl. No.: 16/065,832

(22) PCT Filed: Jan. 13, 2017

(86) PCT No.: PCT/IB2017/050182
§ 371 (c)(1),
(2) Date: Jun. 25, 2018

(87) PCT Pub. No.: WO2017/122163
PCT Pub. Date: Jul. 20, 2017

(65) Prior Publication Data
US 2019/0008564 A1 Jan. 10, 2019

(30) Foreign Application Priority Data
Jan. 15, 2016 (WO) .................. PCT/IB2016/050207

(51) Int. Cl.
| | |
|---|---|
| *A61B 17/28* | (2006.01) |
| *B25B 7/00* | (2006.01) |
| *B25B 27/20* | (2006.01) |
| *A61B 17/02* | (2006.01) |
| *A61B 17/70* | (2006.01) |

(Continued)

(52) U.S. Cl.
CPC ........ *A61B 17/2804* (2013.01); *A61B 17/025* (2013.01); *A61B 17/0206* (2013.01); *A61B 17/2816* (2013.01); *A61B 17/7077* (2013.01); *A61B 17/7083* (2013.01); *B25B 7/00* (2013.01); *B25B 27/20* (2013.01); *B25B 27/205* (2013.01); *A61B 2017/00353* (2013.01); *A61B 2017/00477* (2013.01); *A61B 2017/0256* (2013.01); *A61B 2017/681* (2013.01)

(58) Field of Classification Search
CPC .... B25B 7/00; B25B 7/10; B25B 7/18; B25B 13/5083; B25B 13/54
See application file for complete search history.

(56) References Cited

U.S. PATENT DOCUMENTS 1,122,165 A * 12/1914 Schoening ............ B25B 27/205
81/302
3,681,840 A * 8/1972 Pool ...................... B25B 27/205
29/229

(Continued)

*Primary Examiner* — Nicholas W Woodall
(74) *Attorney, Agent, or Firm* — Andre Roland S.A.; Nikolaus Schibli

(57) ABSTRACT

A dual compression and distraction tool for surgical operations, the tool including a first arm having a first pivot axis, a second pivot axis, a first lever, and a first dual purpose jaw, a second arm having a third pivot axis, a fourth pivot axis, a second lever, and a second dual purpose jaw, wherein, in a first position, the first arm is pivotably connected to the second arm such that the first pivot axis is merged with the third pivot axis, to form an distraction tool, and wherein, in a second position, the first arm is pivotably connected to the second arm such that the second pivot axis is merged with the fourth pivot axis, to form a compression tool.

8 Claims, 3 Drawing Sheets

(51) Int. Cl.
*A61B 17/00* (2006.01)
*A61B 17/68* (2006.01)

(56) References Cited

U.S. PATENT DOCUMENTS

| | | | | |
|---|---|---|---|---|
| 3,762,019 | A * | 10/1973 | Epstein | B25B 27/205 |
| | | | | 29/229 |
| 4,539,873 | A * | 9/1985 | Freed | B25B 9/00 |
| | | | | 29/229 |
| 4,776,245 | A * | 10/1988 | Gustavsson | B25B 27/205 |
| | | | | 29/229 |
| 5,023,989 | A * | 6/1991 | Hargrave | B05B 15/00 |
| | | | | 29/426.5 |
| 5,236,436 | A * | 8/1993 | Koros | A61B 17/062 |
| | | | | 606/148 |
| 5,865,075 | A * | 2/1999 | Medved | B25B 27/205 |
| | | | | 29/229 |
| 6,551,316 | B1 | 4/2003 | Rinner et al. | |
| 10,421,178 | B2 * | 9/2019 | Engel | B25B 7/10 |
| 2005/0245928 | A1 | 11/2005 | Colleran et al. | |
| 2006/0235427 | A1 | 10/2006 | Thomas et al. | |
| 2011/0313460 | A1 | 12/2011 | McLean et al. | |
| 2013/0012999 | A1 | 1/2013 | Petit | |
| 2013/0019720 | A1 * | 1/2013 | Harrison | B25B 27/205 |
| | | | | 81/409.5 |

* cited by examiner

COMBINED DISTRACTION AND COMPRESSION CLAMP FOR SURGICAL OPERATIONS

CROSS-REFERENCE TO RELATED APPLICATIONS

The present application is a United States national stage application of PCT/M2017/050182 filed on Jan. 13, 2017 that designated the United States, and claims foreign priority to International Patent Application PCT/IB2016/050207 filed on Jan. 15, 2016, the contents of both documents being herewith incorporated by references in their entirety.

FIELD OF THE INVENTION

The present invention is related to the field of surgical tools, in particular surgical clamps for distraction and compression of implants, tissue, organs, and bones.

BACKGROUND

In the field of surgical operations, to increase a space between two elements, for example a cut or incision, different types of distraction clamps can be used to expand the skin, different organs, separate bones, etc. Moreover, to hold together two different elements, different types of compression clamps are used, for example, two hold two pieces of fractured bones together, to hold incised tissue together for stitching, etc.

However, quite often one and the same surgical operations requires both compression and distraction of different elements during the surgery, and the background art solutions do not propose a solution to reduce the equipment needed for a surgery. In addition, as the clamps usually have parts that form narrow gaps, for example between two different components of a clamp that are connected together, and also cannot be disassembled into individual components, there are difficulties in cleaning such surgical tools for sterilization. Accordingly, in light of these drawbacks related to the existing clamps, new devices and methods for compression and distraction are desired.

SUMMARY

According to one aspect of the present invention, a dual distraction and compression clamp for surgical operations is provided. Preferably, the tool includes a first arm having a first pivot axis, a second pivot axis, a first lever, and a first dual purpose jaw, and a second arm having a third pivot axis, a fourth pivot axis, a second lever, and a second dual purpose jaw. Moreover, preferably, in a first position, the first arm is pivotably connected to the second arm such that the first pivot axis is merged with the third pivot axis, to form a distraction tool, and in a second position, the first arm is pivotably connected to the second arm such that the second pivot axis is merged with the fourth pivot axis, to form a compression tool.

According to another aspect of the present invention, a method for using a dual compression and distraction tool is provided. Preferably, the tool includes a first arm having a first pivot axis, a second pivot axis, a first lever, and a first dual purpose jaw, and including a second arm having a third pivot axis, a fourth pivot axis, a second lever, and a second dual purpose jaw. Moreover, preferably the method includes the steps of connecting the first arm with the second arm such that the first pivot axis of the first arm, and the third pivot axis of the second arm are joined together, to form an distraction tool, disconnecting the first arm from the second arm, and turning the first arm relative to the second arm by 180° along an axis formed by the longitudinal extension of the first arm. In addition, the method further preferably includes the step of connecting the first arm with the second arm such that the second pivot axis of the first arm, and the fourth pivot axis of the second arm are joined together, to form a compression tool.

The above and other objects, features and advantages of the present invention and the manner of realizing them will become more apparent, and the invention itself will best be understood from a study of the following description with reference to the attached drawings showing some preferred embodiments of the invention.

BRIEF DESCRIPTION OF SEVERAL VIEWS OF THE DRAWINGS

The accompanying drawings, which are incorporated herein and constitute part of this specification, illustrate the presently preferred embodiments of the invention, and together with the general description given above and the detailed description given below, serve to explain features of the invention.

Herein, identical reference numerals are used, where possible, to designate identical elements that are common to the figures. Also, the images are simplified for illustration purposes and may not be depicted to scale.

DESCRIPTION OF THE PREFERRED EMBODIMENTS

Figure 1:
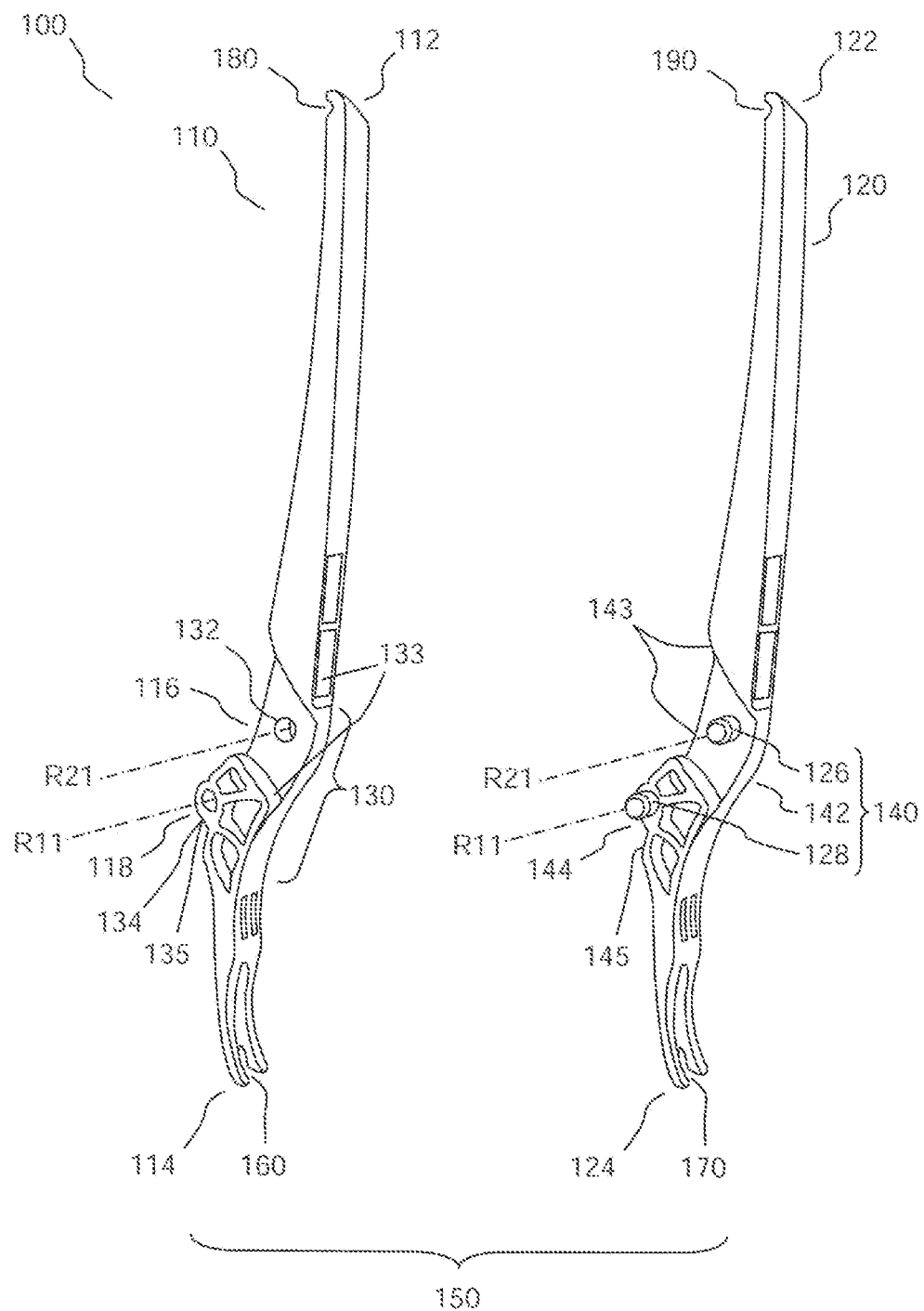
FIG. 1 shows a perspective view of the two arms that form the dual distraction and compression clamp according to one aspect of the present invention.

FIG. 1 shows a perspective view of two main arms 110, 120 that have been separated from each other, the two main arms 110, 120 forming the components of a combined or dual distraction and compression clamp 100, according to one aspect of the present invention. Each arm 110, 120 includes a dual-position engagement mechanism 130, 140, respectively, that permits mutual engagement of the two arms 110, 120 in two different positions. In the variant shown, each dual-position engagement mechanism 130, 140 of the arms 110, 120 includes two pivot axes, labelled as R11 and R21 for arm 110, and labelled R12 and R22 for arm 120. On arm 110 at dual-position engagement mechanism 130, at a location of pivot axis R11, a through hole 118 is formed, and at a location of pivot axis R21, a through hole 116 is formed. Analogously, on arm 120 at dual-position engagement mechanism 140, at a location of pivot axis R12 a bolt 128 is formed, and at location of pivot axis R22, a bolt 126 is formed. In a first position, bolt 128 of arm 120 is configured to engage and penetrate into hole 118 of arm 110, so that axis R11 and R12 are merged, and in a second position, bolt 126 of arm 120 is configured to engage and penetrate into hole 116 of arm 110, so that axis R21 and R22 are merged.

At one extremity of arms 110, 120, a clamp 150 can be formed with corresponding jaws 114, 124, and the clamp 150 with jaws 114, 124 can be used to and is configured for expanding operations, when the clamp 150 is in the first position, and can be used to and configured for compressing operations, when the clamp 150 is in the second position. The clamp 150, whether in the first position or in the second position, can be operated by a user via the levers 112, 122 of arms 110, 120. As can be seen from FIG. 1, both arms can be made to have exactly the same shape and dimensions, and therefore can be made from the same mold, but for the presence of bolts 126, 128 of arm 120 that are fixedly lodged into holes of arm 120 that correspond to the holes 116, 118 of arm 110.

In this respect, in the variant shown in FIG. 1, the dual distraction and compression clamp 100 can be made solely of four elements: Two arms 110, 120 that can have exactly the same dimensions and shape, and two bolts 126, 128 that are fixedly attached to one arm 120. The bolts 126, 128 are made such that they can engage fixedly into one arm once pressed into a corresponding hole, and on the other hand can removably engage into the other arm. Also, in a variant the bolts 126, 128 are made that they can snap into all the holes 116, 118, and the holes that correspond to bolts 126, 128, and can also be removed from all the holes, for easier sterilization of the arms 110, 120. Thereby, bolts 126, 128 can have a symmetrical design for snapping into corresponding holes on both end sides, and all the holes can also have the same complementary design to correspond to the bolts for snap-in. This allows to disassemble the combined distraction and compression clamp 100 into the basic parts, including two arms 110, 120, and two bolts 126, 128 that are removed from the arms, for easier and more thorough sterilization and cleaning, as the disassembly avoids any small gaps and cavities that would prevent sterilization. Also, with the snap-in mechanism, the clamp 100 can be easily configured for both compression and distraction, as discussed further below.

Figure 2:
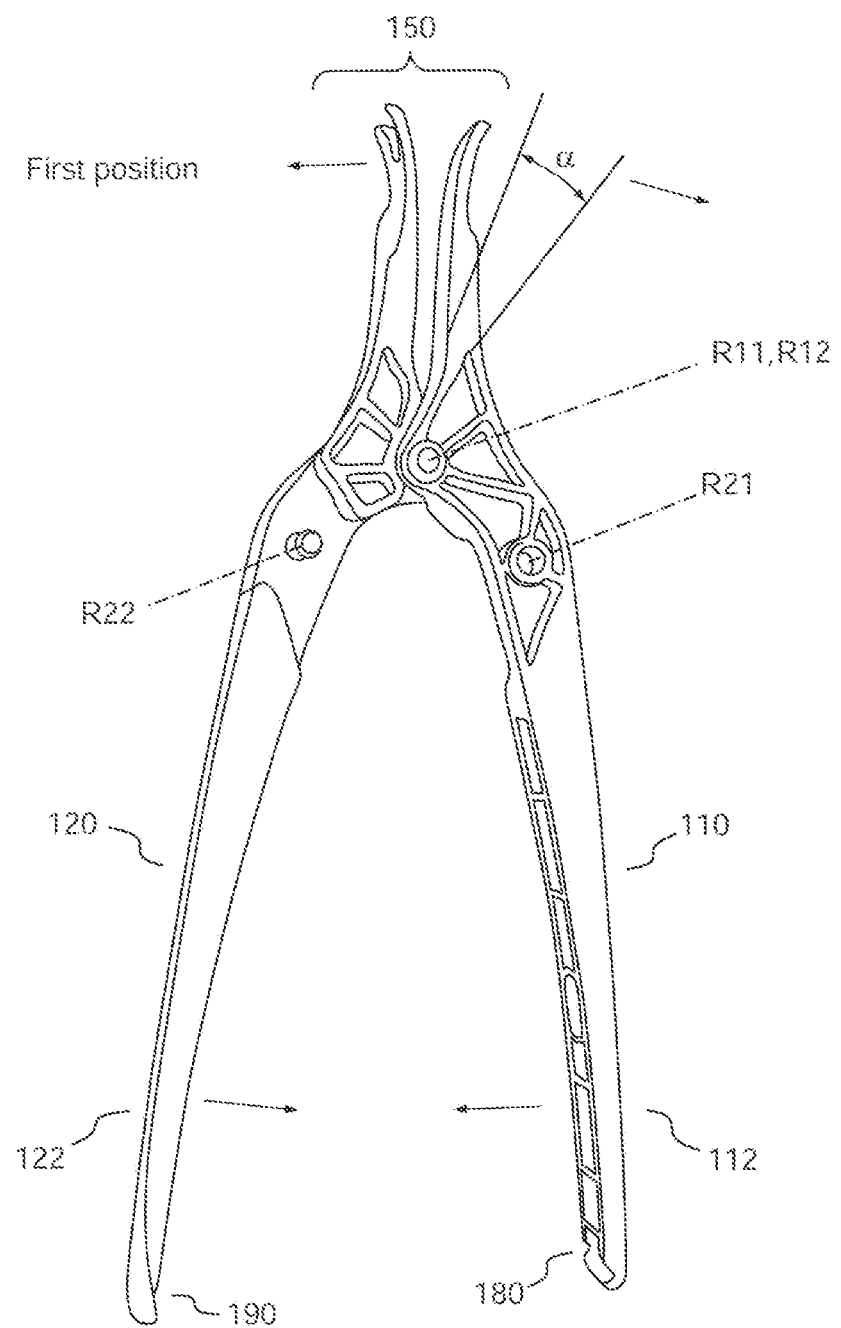
FIG. 2 shows a perspective view of the clamp in the first position for distraction action according to another aspect of the present invention.

FIG. 2 shows a perspective view of the combined distraction and compression clamp 100, in which the clamp 100 is in the first position, configured as an distraction clamp. Axes R11 and R12 are merged by inserting bolt 128 into hole 118. For this operation, arm 120 as shown in FIG. 1 is turned about an axis of longitudinal extension by about 180° relative to the arm 110 in a clockwise direction when viewed in the axis of longitudinal extension towards the jaw 124, so that bolt 128 can be engaged with hole 118. In the first position, arm 110 and arm 120 can pivot relative to each other around pivot axes R11, R12 that are merged, so that levers 112 and 122 of arms 110, 120, respectively can be operated by a user's hand. In this respect, by compression of levers 112, 122, for example by a user's hands, the jaws 114, 124 perform a distraction action. Jaws 114, 124 are configured such that they form an arc that are bent away from each other.

In the variant shown, bolt 128 has snapped into hole 118, and hole cavity 134 at hole 118 of arm 110 has engaged with a motion limiting cavity 144 around bolt 128 of arm 120. Hole cavity 134 and motion limiting cavity 144 serve two purposes. First, by providing for space to engage bolt 128 with hole 118, the arms 110 and 120 can be arranged next to each other without any offset when viewed in a direction that is parallel to pivot axis R11, R12, R21, R22. Thereby, jaws 114, 124 of clamp 150 will face each other aligned. Second, side wall 145 of cavity 144, and side wall 135 around hole 118 are configured to such to allow a certain relative pivoting motion between arm 110 and arm 120 by angle α, the motional range of the clamp in the first position can be defined, by providing for a mutual abutment surface with side wall 135 that engages with side wall 145.

Figure 3:
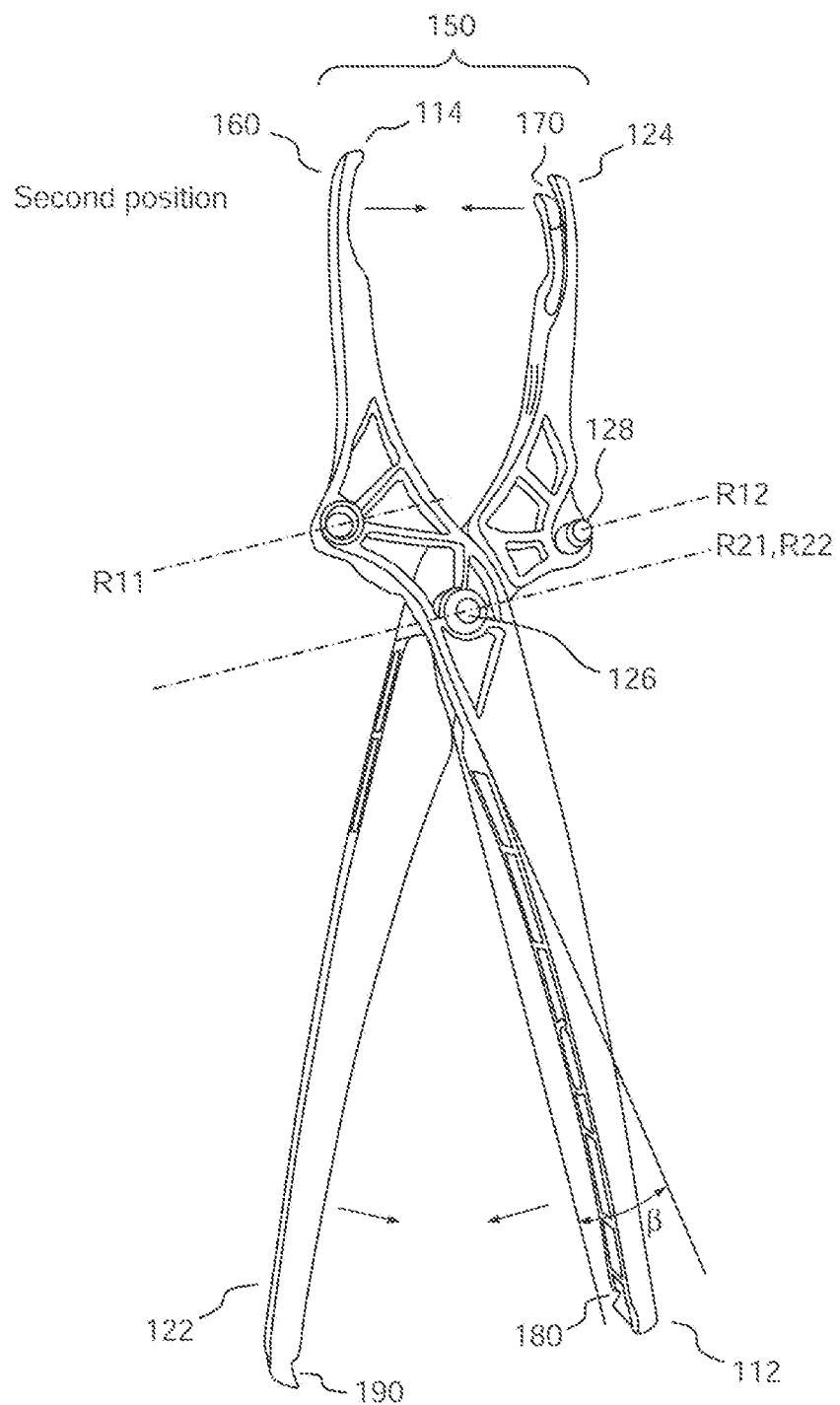
FIG. 3 shows a perspective view of the clamp in the second position for compression action according to still another aspect of the present invention.

FIG. 3 shows a perspective view of the combined distraction and compression clamp 100, in which the clamp 100 is in the second position, serving as a compression clamp. Axes R21 and R22 are merged by inserting bolt 126 into hole 116. For this operation, arm 120 as shown in FIG. 1 is turned about an axis of longitudinal extension by about 180° relative to the arm 110 in a counter-clockwise direction when viewed in the axis of longitudinal extension towards the jaw 124, so that bolt 126 can be engaged with hole 116. In this second position, arm 110 and arm 120 can pivot relative to each other around pivot axes R21, R22 that are merged, so that levers 112 and 122 of arms 110, 120, respectively can be operated by a user's hand. In this respect, by compression of levers 112, 122, for example by a user's hand, the jaws 114, 124 perform a compression action. As compared to the first position, the jaws 114, 124 face each other from the opposite side different side. Jaws 114, 124 are configured such that they form an arc that are bent towards each other.

In the variant shown, bolt 126 has snapped into hole 116, and hole cavity 132 at hole 116 of arm 110 has engaged with a motion limiting cavity 142 around bolt 126 of arm 120. Hole cavity 132 and motion limiting cavity 142 can have the same dimensions and shape, serve two purposes. First, by providing for space to engage bolt 126 with hole 116, the arms 110 and 120 can be arranged next to each other without any offset when viewed in a direction that is parallel to pivot axis R11, R12, R21, R22. Thereby, jaws 114, 124 of clamp 150 will face each other aligned, as explained above with respect to FIG. 2. Second, side wall 143 of cavity 142 and side wall 133 of cavity 142 around hole 116 are configured to such to allow a certain relative pivoting motion between arm 110 and arm 120 by angle β, such that the motional range of the clamp 150 in the second position can be defined, by providing for a mutual abutment surface with side wall 133 that engages with side wall 143.

Moreover, the jaws 114, 124 of clamp 150 are also equipped with grooves 160, 170, respectively. By the presence of grooves 160, 170 in clamp, it is further possible to facilitate the grabbing of articles and devices when the distraction and compression clamp 100 is in a second position. In addition, tip ends of levers 112 and 122 of arms 110, 120, respectively can be also equipped with grooves 180, 190, respectively. In the variant shown, grooves 180, 190 are formed as semi-cylindrical cavities with an axis in parallel to the pivot axis R11, R12, R21, R22. With these groove 180, 190, for example in the first position, it is possible to use the distraction and compression clamp 100 to grab elements during the surgery, for example rods having a complementary shape or other devices.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

The invention claimed is:
1. A dual compression and distraction tool for surgical operations, the tool comprising:
 a first arm having a first pivot axis, a second pivot axis, a first lever, and a first dual purpose jaw; and
 a second arm having a third pivot axis, a fourth pivot axis, a second lever, and a second dual purpose jaw, wherein, in a first position, the first arm is pivotably connected to the second arm such that the first pivot axis is merged with the third pivot axis, to form a distraction tool, wherein, in a second position, the first arm is pivotably connected to the second arm such that the second pivot axis is merged with the fourth pivot axis, to form a compression tool, and wherein the first and the third pivot axis includes a corresponding hole and connection bolt pair, and the second and the fourth pivot axis includes a corresponding hole and connection bolt pair.

2. The dual compression and distraction tool according to claim 1, wherein the first and second pivot axis of the first arm each include the hole, and the third and fourth pivot axis of the second arm each include the corresponding connection bolt.

3. A method for using a dual compression and distraction tool, the tool including a first arm having a first pivot axis, a second pivot axis, a first lever, and a first dual purpose jaw, and including a second arm having a third pivot axis, a fourth pivot axis, a second lever, and a second dual purpose jaw, the method comprising the steps of:

connecting the first arm with the second arm such that the first pivot axis of the first arm, and the third pivot axis of the second arm are joined together, to form an distraction tool;

disconnecting the first arm from the second arm;

turning the first arm relative to the second arm by 180° along an axis formed by the longitudinal extension of the first arm; and connecting the first arm with the second arm such that the second pivot axis of the first arm, and the fourth pivot axis of the second arm are joined together, to form a compression tool.

4. The dual compression and distraction tool according to claim 1, wherein the first arm and the second arm have a same shape and dimensions.

5. The dual compression and distraction tool according to claim 1, wherein the first and second pivot axis of the first arm each include the connection bolt, and the third and fourth pivot axis of the second arm each include the corresponding hole.

6. The dual compression and distraction tool according to claim 2, wherein the connection bolts of the third and fourth pivot axis and the through holes of the first and second pivot axis are configured to form releasable snap-in mechanisms.

7. The method for using a dual compression and distraction tool according to claim 3, wherein in the steps of connecting the first arm with the second arm, the first arm is rotatably attached to the second arm by snap-in mechanisms arranged at the first pivot axis of the first arm and at the third pivot axis of the second arm, and at the second pivot axis of the first arm and the fourth pivot axis of the second arm.

8. The method for using a dual compression and distraction tool according to claim 3, wherein through holes are formed at the first and second pivot axis of the first arm, and connection bolts are formed at the third and fourth pivot axis of the second arm.

\* \* \* \* \*